United States Patent
Danzer et al.

US008501414B2

(10) Patent No.: US 8,501,414 B2
(45) Date of Patent: Aug. 6, 2013

(54) DETECTION OF BACTERIA

(75) Inventors: Martin Danzer, Altmünster (AT); Helene Polin, Attnang-Puchheim (AT); Katja Hofer, Ottensheim (AT); Brigitte Fiedler, Ansfelden (AT); Juliane Radler, St. Johann/Wbg. (AT); Katrin Rosenhammer, Linz (AT); Sabine Atzmüller, St. Veit im Mühlkreis (AT); Christian Gabriel, Altenberg (AT)

(73) Assignee: Österreichisches Rotes Kreuz Landesverband Oberösterreich (AT)

( * ) Notice: Subject to any disclaimer, the term of this patent is extended or adjusted under 35 U.S.C. 154(b) by 767 days.

(21) Appl. No.: 12/310,874

(22) PCT Filed: Sep. 4, 2007

(86) PCT No.: PCT/AT2007/000420
§ 371 (c)(1),
(2), (4) Date: Nov. 19, 2009

(87) PCT Pub. No.: WO2008/028210
PCT Pub. Date: Mar. 13, 2008

(65) Prior Publication Data
US 2011/0076673 A1     Mar. 31, 2011

(30) Foreign Application Priority Data

Sep. 7, 2006 (AT) ................ A 1496/2006

(51) Int. Cl.
*C12Q 1/68* (2006.01)
*C07H 21/04* (2006.01)

(52) U.S. Cl.
USPC ..... 435/6.15; 435/6.11; 435/6.12; 536/24.32; 536/24.33

(58) Field of Classification Search
None
See application file for complete search history.

(56) References Cited

U.S. PATENT DOCUMENTS

| | | | |
|---|---|---|---|
| 5,994,066 | A | 11/1999 | Bergeron et al. |
| 6,001,564 | A | 12/1999 | Bergeron et al. |
| 6,664,081 | B2 | 12/2003 | Brentano et al. |
| 7,169,555 | B2 * | 1/2007 | Stuber et al. ........ 435/6.14 |
| 2005/0037408 | A1 | 2/2005 | Christensen et al. |

FOREIGN PATENT DOCUMENTS

| | | |
|---|---|---|
| EP | 1366195 B1 | 12/2003 |
| EP | 1473370 | 11/2004 |
| WO | 9303186 A1 | 2/1993 |
| WO | 9815648 A1 | 4/1998 |
| WO | WO 9947706 A1 * | 9/1999 |
| WO | 0052203 A2 | 9/2000 |
| WO | 0210444 | 2/2002 |
| WO | 02070728 | 9/2002 |
| WO | 02070736 A2 | 9/2002 |
| WO | 2004046375 | 6/2004 |

OTHER PUBLICATIONS

Lopez, I. et al. Applied and Environmental Microbiology 69(11):6801-6807 (Nov. 2003).*
International Search Report, PCT/AT2007/000420, Jun. 30, 2008.

* cited by examiner

*Primary Examiner* — Diana Johannsen
(74) *Attorney, Agent, or Firm* — Lerner, David, Littenberg, Krumholz & Mentlik, LLP

(57) ABSTRACT

The invention relates to a method for detecting bacterial contaminations preferably in physiological samples as well as sequences of synthetic oligonucleotides used therefor. The method comprises the steps of i) extracting the nucleic acid, particularly bacterial DNA, ii) amplification by means of primers and detection by means of oligonucleotides, particularly fluorescence-marked oligonucleotides as hybridization probes, containing a sequence that is selected from among a group encompassing SEQ ID NO:5 to SEQ ID NO:35, preferably in real-time PCR, and iii) evaluation by means of fusion curve analysis.

14 Claims, No Drawings

DETECTION OF BACTERIA

CROSS REFERENCE TO RELATED APPLICATIONS

The present application is a national phase entry under 35 U.S.C. §371 of International Application No. PCT/AT2007/000420, filed Sep. 4, 2007, published in German, which claims the benefit of Austrian Patent Application No. A 1496/2006, filed Sep. 7, 2006.

SEQUENCE LISTING

The instant application contains a Sequence Listing which has been submitted in ASCII format via EFS-Web and is hereby incorporated by reference in its entirety. Said ASCII copy, created on Dec. 1, 2010, is named ABP3.341.txt and is 8,328 bytes in size.

The present invention describes oligonucleotide sequences for detecting bacterial contaminations with a length of 10 to 30 bases, a method for detecting at least one bacterial contamination as well as a kit for detecting bacterial contaminations, respectively preferably in a physiological sample.

The invention relates to the field of molecular biology and its application in clinical diagnostics. More precisely, the invention relates to a method and reagents for amplifying and for detecting nucleic acids of bacteria. The invention therefore is applied for detecting bacteria, groups of bacteria and types of bacteria, generally in the field of clinical diagnostics and the field of molecular biology.

In the area of medicine, in particular in the clinical area, bacterial contaminations pose a big threat for the patients. In particular upon providing blood preservations and the components extracted therefrom, like for example blood plasma for producing diverse drugs or thrombocyte concentrates, it has to be strictly observed to exclude bacterial contaminations with the highest possible security. Such bacterial contaminations may, for example, cause serious septic reactions in patients.

PCR is a method for amplifying specific nucleic acid sequences and enables the quick detection of nucleic acids present in a sample, which prior to that were present in a non-detectably low amount.

The detection of nucleic acid molecules in a sample is required in the most different areas, for example in medicine, quality management, research, etc. In that, it may often also be necessary to detect several nucleic acid molecules different from one another in a single sample. Here, for reasons of time and costs, it is desirable to simultaneously detect the various nucleic acid molecules in the sample.

However, the highly sensitive, molecular biological detection of bacteria by means of polymerase chain reaction (PCR) in blood is frequently impaired due to the low cell count in proportion to the sample volume. Additionally, false-positive results may occur by amplification of non-specific sequences of the human DNA background. PCR is a method for amplifying specific nucleic acid sequences and enables the quick detection of nucleic acids present in a sample, which prior to that were present in a non-detectably low amount.

The detection of nucleic acid molecules in a sample is required in the most different areas, for example in medicine, quality management, research, etc. In that, it may often also be necessary to detect several nucleic acid molecules different from one another in a single sample. Here, for reasons of time and costs, it is desirable to simultaneously detect the various nucleic acid molecules in the sample.

Thus, for example, EP 1 366 195 B1 describes a method for simultaneous detection of at least two nucleic acid molecules different from one another in one sample, whereat in a first step, a multiplex PCR, and in a second step, a hybridization reaction are performed with probes immobilized on a microarray, whereupon the hybridized PCR products are detected and, if necessary, quantified, as well as a microarray and a kit for simultaneous detection of at least two nucleic acid molecules different from one another in one sample. The probes used for the hybridization reaction, which respectively hybridize specifically from the amplified sequences of the nucleic acid molecules differing from one another, have fusion temperatures deviating from one another by a maximum of 2° C., preferably a maximum of 1° C. Due to the fact that the fusion temperatures of the probes used for the hybridization reaction differ from one another by a maximum of 2° C., it is possible to simultaneously detect a high number of nucleic acid molecules in one sample, since for the hybridization reaction, the same conditions are set for all probes in respect of temperature, but also salt concentration, pH-value, etc.

Furthermore, e.g., U.S. Pat. No. 6,664,081 B2 describes a method, oligonucleotides and a kit for detecting types of mycobacteria using the oligonucleotides according to the invention for in-vitro amplification of the 16S rRNA sequences for many types of the genus *mycobacterium*.

The object of the present invention is to provide a method and reagents enabling a sensitive and specific detection of bacterial contaminations, preferably in physiological samples.

The object is respectively solved independently by oligonucleotides with a nucleotide sequence complementary to a nucleotide sequence coding for a sequence of the highly conserved 16S rDNA region of a bacteria genome, wherein the oligonucleotide has at least 10 consecutive bases of a sequence selected from a group encompassing SEQ ID NO:5 to SEQ ID NO:35, a method comprising the steps of i) extracting the nucleic acid, particularly bacterial DNA, ii) amplification by means of primers and detection by means of oligonucleotides, particularly fluorescence-marked oligonucleotides as hybridization probes according to any of the claims 1 to 26 in real-time PCR, and iii) evaluation by means of fusion curve analysis, and a kit containing at least one primer pair for amplification, preferably according to claims 32 and/or 35, and at least one oligonucleotide according to any of the claims 1 to 26, a thermally stable DNA polymerase and dNTP solutions, if necessary. The selection of the bacteria-specific oligonucleotides according to the invention as hybridization probes guarantees the detection of a total of approx. 230 pathogenic bacteria. The sensitivity of the method is guaranteed by the selection of specific primers for the amplification of nucleic acid sequences in the highly conserved 16S rDNA region and the specificity by the oligonucleotides according to the invention.

In that, it is particularly advantageous to perform a 5' and/or 3' modification, in particular by means of fluorescence marking, in order to enable a simple detection, by which the addition of further reagents and thus repeated opening of the reaction vessel can be avoided.

Preferably, with oligonucleotides selected from a group encompassing SEQ ID NO:5, SEQ ID NO:6 to SEQ ID NO:8, SEQ ID NO:13 to SEQ ID NO:15, SEQ ID NO:28, SEQ ID NO:29 and SEQ ID NO:31, gram-positive types of bacteria, and with oligonucleotides selected from a group encompassing SEQ ID NO:5, SEQ ID NO:9 to SEQ ID NO:11, SEQ ID NO:16 to SEQ ID NO:27, SEQ ID NO:30 and SEQ ID NO:32 to SEQ ID NO:35, gram-negative types of bacteria are detected. Thus, in advance already, a classification into gram-positive or gram-negative types of bacteria can take place.

In that, it is particularly favorable that oligonucleotide SEQ ID NO:6 is specific for the genera *Enterococcus, Kurthia, Lactobacillus* and/or *Listeria* and selectively detects *Enterococcus avium, Enterococcus casseliflavus, Enterococcus durans, Enterococcus faecalis, Enterococcus faecium, Enterococcus gallinarum, Enterococcus hirae, Kurthia gibsonii, Kurthia sibirica, Lactobacillus acidophilus, Lactobacillus casei, Lactobacillus fermentum, Lactobacillus plantarum, Lactobacillus salivarius, Listeria monocytogenes* and/or *Listeria pyogenes*, preferably in a physiological sample.

It is furthermore advantageous that oligonucleotide SEQ ID NO:7 is specific for the genera *Leuconostoc* and/or *Streptococcus* and selectively detects *Leuconostoc citreum, Leuconostoc lactis, Streptococcus agalactiae, Streptococcus anginosus, Streptococcus bovis, Streptococcus mitis, Streptococcus pneumoniae, Streptococcus pyogenes, Streptococcus salivarius, Streptococcus sanguinis* and/or *Streptococcus* sp., preferably in a physiological sample.

Oligonucleotide SEQ ID NO:8 is advantageously specific for the genera *Bacillus, Clostridium, Mycoplasma* and/or *Staphylococcus* and selectively detects *Bacillus anthracis, Bacillus circulans, Bacillus pumilus, Bacillus sphaericus, Bacillus subtilis, Bacteroides capillosus, Brevibacillus laterosporus, Clostridium bifermentans, Clostridium botulinum, Clostridium butyricum, Clostridium clostridioforme, Clostridium difficile, Clostridium novyi, Clostridium perfringens, Clostridium septicum, Clostridium sporogenes, Clostridium tetani, Erysipelothrix rhusiopathiae, Fusobacterium alocis, Gemella haemolysans, Mycoplasma orale, Mycoplasma pulmonis, Mycoplasma buccale, Staphylococcus aureus, Staphylococcus capitis, Staphylococcus cohnii, Staphylococcus epidermidis, Staphylococcus haemolyticus, Staphylococcus hominis, Staphylococcus lugdunensis, Staphylococcus xylosus* and/or *Veillonella parvula*, preferably in a physiological sample.

Oligonucleotide SEQ ID NO:9 is preferably specific for the genera *Acinetobacter, Actinomyces, Aeromonas, Anaerobiospirillum, Bartonella, Brucella, Citrobacter, Enterobacter, Haemophilus, Klebsiella, Kluyvera, Legionella, Pasteurella, Proteus, Rickettsia, Salmonella, Serratia, Shigella, Vibrio, Yersinia* and selectively detects *Acinetobacter baumannii, Acinetobacter calcoaceticus, Acinetobacter haemolyticus, Acinetobacter johnsonii, Acinetobacter junii, Acinetobacter lwoffii, Actinomyces meyeri, Actinomyces pyogenes, Aeromonas caciae, Aeromonas hydrophila, Aeromonas schubertii, Aeromonas veronii, Agrobacterium radiobacter, Alcaligenes faecalis, Anaerobiospirillum succiniciproducens, Anaerobiospirillum thomasii, Acranobacterium pyogenes, Bartonella bacilliformis, Bartonella henselae, Brucella abortus, Brucella melitensis, Calymmatobacterium granulomatis, Citrobacter amalonaticus, Citrobacter freundii, Coxiella burnetti, Edwardsiella tarda, Enterobacter aerogenes, Enterobacter cloacae, Enterobacter sakazakii, Enterobacter* sp., *Escherichia coli, Haemophilus aegypticus, Haemophilus aphrophilus, Haemophilus ducreyi, Haemophilus parahaemolyticus, Haemophilus parainfluenzae, Haemophilus paraphrophilus, Haemophilus segnis, Hafnia alvei, Klebsiella oxytoca, Klebsiella pneumoniae, Klebsiella rhinoscleromatis, Kluyvera ascorbata, Kluyvera cryocrescens, Legionella dumoffii, Legionella micdadei, Morganella morganii, Ochrobactrum anthropi, Pantoea agglomerans, Pasteurella gallinarum, Pasteurella pneumotropica, Plesiomonas shigelloides, Propionibacterium acnes, Proteus mirabilis, Proteus penneri, Proteus vulgaris, Pseudomonas putida, Rickettsia akari, Rickettsia australis, Rickettsia conorii, Salmonella choleraesius, Salmonella enterica, Salmonella paratyphi A, Salmonella paratyphi B, paratyphi C, Salmonella typhi, Salmonella typhinurium, Serratia ficaria, Serratia fonticola, Serratia grimesii, Serratia liquefaciens, Serratia marcescens, Serratia rudidaea, Shigella boydii, Shigella dysenteriae, Shigella flexneri, Shigella sonnei, Vibrio alginolyticus, Vibrio hollisae, Wigglesworthia glossinidia, Xanthomonas campestris, Yersinia enterocolitica, Yersinia pestis* and/or *Yersinia pseudotuberculosis*, preferably in a physiological sample.

In that, it is favorable that oligonucleotide SEQ ID NO:10 is specific for the genera *Achromobacter, Actinomadura, Actinomyces, Afipia, Bordetella, Burkholderia, Campylobacter, Capnocytophaga, Comamonas, Corynebacterium, Ehrlichia, Fusobacterium, Methylobacterium, Mycobacterium, Neisseria, Nocardia, Oligella, Prevotella* and/or *Rhodococcus* and selectively detects *Achromobacter piechaudii, Achromobacter xylosoxidans, Actinomadura madurae, Actinomadura pelletieri, Actinomyces bovis, Actinomyces naeslundii, Actinomyces viscosus, Afipia broomeae, Afipia felis, Bacteroides gracilis, Bilophila wadsworthia, Bordetella bronchiseptica, Bordetella parapertussis, Bordetella pertussis, Burkholderia cepacia, Burkholderia gladioli, Burkholderia mallei, Burkholderia pseudomallei, Campylobacter coli, Campylobacter fetus, Campylobacter jejuni, Campylobacter lari, Capnocytophaga canimorsus, Capnocytophaga cynodegmi, Capnocytophaga gingivalis, Capnocytophaga ochracea, Capnocytophaga sputigena, Chromobacterium violaceum, Comamonas terrigena, Comamonas testosteroni, Corynebacterium diphteriae, Corynebacterium minutissimum, Corynebacterium pseudotuberculosis, Corynebacterium urealyticum, Ehrlichia canis, Ehrlichia chaffeensis, Ehrlichia sennetsu, Eikenella corrodens, Eubacterium lentum, Francisella tularensis, Fusobacterium necrophorum, Fusobacterium nucleatum, Gardnerella vaginalis, Haemophilus influenzae, Helicobacter pylori, Kingella kingae, Methylobacterium extorquens, Methylobacterium mesophilicun, Mycobacterium africanum, Mycobacterium avium, Mycobacterium bovis, Mycobacterium chelonae, Mycobacterium intracellulare, Mycobacterium kanasasii, Mycobacterium leprae, Mycobacterium malmoense, Mycobacterium marinum, Mycobacterium scrofulaceum, Mycobacterium tuberculosis, Mycobacterium xenopi, Neisseria cinerea, Neisseria gonorrhoeae, Neisseria meningitidis, Nocardia asteroides, Nocardia nova, Nocardia octitidiscaviarum, Oligella urethralis, Oligella ureulytica, Peptoniphilus asaccharolyticus, Peptostreptococcus prevotii, Porohyromonas gingivalis, Prevotella buccae, Prevotella buccalis, Prevotella corporis, Prevotella denticola, Prevotella oralis, Rhodococcus equi, Rhodococcus erythropolis, Rhodococcus rhodochrous, Stenotrophomonas maltophilia, Streptobacillus moniliformis, Tropheryma whippley* and/or *Weeksella virosa*, preferably in a physiological sample.

Oligonucleotide SEQ ID NO:11 is advantageously specific for the genera *Actinobacillus, Borrelia, Legionella, Moraxella (Branhamella), Providencia, Pseudomonas* and/or *Vibrio* and selectively detects *Actinobacillus actinomycetemcomitans, Actinobacillus equuli, Actinobacillus hominis, Actinobacillus suis, Actinobacillus ureae, Borrelia afzelii, Borrelia burgdorferi, Borrelia garninii, Borrelia hermsii, Borrelia hispanica, Chryseomonas luteola, Legionella dumoffii, Legionella micdadei, Legionella pneumophila, Moraxella (Branhamella) catarrhalis, Moraxella (Branhamella) nonliquefaciens, Moraxella (Branhamella) osloensis, Moraxella (Branhamella) phenylpyruvica, Pediococcus pentosaceus, Porphyromonas asaccharolytica, Providencia alcalifaciens, Providencia rettgeri, Providencia rustigianii, Providencia stuartii, Pseudomonas aeruginosa, Pseudomonas fluorescense, Psychrobacter immobilis, Vibrio cholerae, Vibrio parahaemolyticus and/or Vibrio vulnificus, preferably in a physiological sample.

It is advantageous that oligonucleotides SEQ ID NO:13 and SEQ ID NO:14 are specific for the genus Actinomyces and SEQ ID NO:13 selectively detects Actinomyces israelii and SEQ ID NO:14 selectively detects Actinomyces odontolyticus, and Oligonucleotide SEQ ID NO:15 is specific for the genus Arcanobacterium and selectively detects Arcanobacterium haemolyticum, preferably in a physiological sample.

Oligonucleotides SEQ ID NO:16 to SEQ ID NO:20 are advantageously specific for the genus Bacteroides, wherein SEQ ID NO:16 selectively detects Bacteroides eggerthii, SEQ ID NO:17 selectively detects Bacteroides fragilis, SEQ ID NO:18 selectively detects Bacteroides forsythus, SEQ ID NO:19 selectively detects Bacteroides merdae and SEQ ID NO:20 selectively detects Bacteroides putredinis, preferably in a physiological sample.

Oligonucleotides SEQ ID NO:21 and SEQ ID NO:22 are specific for the genus Chlamydiae and SEQ ID NO:21 selectively detects Chlamydiae trachomatis and SEQ ID NO:22 selectively detects Chlamydiae pneumoniae, preferably in a physiological sample.

Oligonucleotide SEQ ID NO:23 is specific for the genus Fusobacterium and selectively detects Fusobacterium sulci, and Oligonucleotides SEQ ID NO:24 and SEQ ID NO:25 are specific for the genus Leptospira and SEQ ID NO:24 selectively detects Leptospira biflexa and SEQ ID NO:25 selectively detects Leptospira interrogans, respectively preferably in a physiological sample.

Oligonucleotide SEQ ID NO:26 is specific for the genus Mobiluncus and selectively detects Mobiluncus mulieris, and Oligonucleotide SEQ ID NO:27 is specific for the genus Mycoplasma and selectively detects Mycoplasma pneumoniae, respectively preferably in a physiological sample.

Oligonucleotides SEQ ID NO:28 and SEQ ID NO:29 are preferably specific for the genus Peptostreptococcus and SEQ ID NO:28 selectively detects Peptostreptococcus anaerobicus and SEQ ID NO:29 selectively detects Peptostreptococcus magnus, preferably in a physiological sample.

It is advantageous that oligonucleotide SEQ ID NO:30 is specific for the genus Porphyromonas and selectively detects Porphyromonas endodontalis, and oligonucleotide SEQ ID NO:31 is specific for the genus Rothia and selectively detects Rothia dentocariosa, preferably in a physiological sample.

Oligonucleotides SEQ ID NO:32 and SEQ ID NO:33 are specific for the genus Sphingobacterium and SEQ ID NO:32 selectively detects Sphingobacterium multivorum and SEQ ID NO:33 selectively detects Sphingobacterium spiritovorum, preferably in a physiological sample.

In that, it proves favorable that oligonucleotide SEQ ID NO:34 is specific for the genus Treponema and selectively detects Treponema pallidum, and Oligonucleotide SEQ ID NO:35 is specific for the genus Ureaplasma and selectively detects Ureaplasma urealyticum, preferably in a physiological sample.

The oligonucleotides of SEQ ID NO:5 to SEQ ID NO:35 prove to be particularly advantageous, because therewith types of bacteria can be specifically detected and furthermore an allocation to certain genera of bacteria may take place.

It also proves advantageous that the oligonucleotides SEQ ID NO:5 to SEQ ID NO:35 can have nucleotide sequences complementary to the oligonucleotide sequences according to the invention, whereby the oligonucleotide can bind to both strands of the DNA double-strand and thus each of the two strands of the DNA sequence of contaminating bacteria can be detected in a biological sample.

According to a further aspect, the present invention relates to a composition comprising a combination of oligonucleotides for detecting bacteria DNA coding for a sequence of the highly conserved 16S rDNA region, wherein the first oligonucleotide has at least 10 consecutive bases of the oligonucleotides SEQ ID NO:5 and is marked with fluorescein at the 3' terminus, and the further oligonucleotide has at least 10 consecutive bases of at least one of the oligonucleotides SEQ ID NO:6 to SEQ ID NO:35 and is marked with a fluorescent dye at the 5' terminus, whereby it is advantageous that the fluorescence-resonance energy transfer (FRET) principle may be used. The two hybridization probes bind to the sought target DNA in spatial proximity and the fluorescein of the first hybridization probe transfers the energy to the adjacent second fluorescent dye, which now emits fluorescence, the intensity of which in sum is directly proportional to the amount of target DNA.

Real-time PCR enables amplification as well as detection in the same closed reaction vessel, whereby the risk of transferring a contamination from one reaction vessel to the other as well as the time requirement arising for opening and closing the reaction vessels or repipetting the amplificate, respectively, are reduced. The real-time PCR according to the invention for detecting bacteria in physiological samples is furthermore characterized by its high robustness and high readiness to be used in day to day operations. In comparison to cultivation methods, there are no significant differences, whereas the real-time PCR method provides a faster result than cultivation. Using PCR, pathogens, which cannot be cultivated or pathogens, which grow very slowly, respectively, too, can be detected timely and very sensitively.

Using the oligonucleotides with a length of at least 10 consecutive bases of the oligonucleotides SEQ ID NO:1 and SEQ ID NO:2 as primers advantageously enables that highly conserved sequences of various strains and types of bacteria can be amplified with primers of the same sequence.

Preferably, controls are included, like an internal control from extraction on and at least one negative and positive control, in particular during amplification. Thereby, false-positive and false-negative results caused by a malfunction or contamination can be excluded.

Preferably, the at least one positive control contains a nucleic acid sequence of Salmonella choleraesius, Pseudomonas aeruginosa and/or Staphylococcus epidermidis, whereby it is guaranteed that with a failure-free procedure, a signal can be detected for the positive controls in any case, and thus a conclusion to the functioning of extraction, amplification and detection is admissible.

In that, it is particularly advantageous, when the nucleic acid sequence of the at least one internal control is amplified with a primer pair consisting of an oligonucleotide with a length of at least 10 consecutive bases of the oligonucleotides SEQ ID NO:3 and SEQ ID NO:4, whereby nucleic acid sequences of the internal control are detected, which are added from extraction on already and are co-amplified, and thus also serve as a workflow control. Thereby, for example, a variation in extraction or insufficient amplification can be detected as well.

In that, the nucleic acid sequences of the internal control are preferably hybridized with an oligonucleotide with a length of at least 10 consecutive bases of the oligonucleotide SEQ ID NO:12 or its complementary sequence, whereby the internal control, too, can be amplified and in particular detected with the same method. By adding the internal control from extraction on it is possible to check the entire process, starting with extraction up to hybridization. In addition, the amplificate of the internal control is characterized by a length of approx. 60 base pairs.

Real-time PCR is performed in capillary tubes, whereby a further advantage of this method is that the PCR reaction vessels do not have to be opened anymore following amplification, since the measurements and quantification are completed following termination of the PCR reaction. Thus, the partially laborious application of the PCR products onto a gel is no longer required and, what is even more important, the risk of carryover contaminations by PCR products, which for diagnostic PCR are one of the main contamination sources, no longer arises.

Preferably, an incubation of the physiological sample with an enzyme solution, in particular lysostaphin-lysozyme solution, is performed prior to extraction, in order to increase the sensitivity for the detection of difficultly digestible gram-positive bacteria.

For extraction, the cells are lysed, bacterial DNA is released, the DNA is bound to magnetized particles, purified, and in a final step eluted with a buffer, whereby standardized methods for purification of the contaminating nucleic acid sequence can be used for the method according to the invention and thus cost-effective methods are available.

Preferably, an incubation of the physiological sample with an enzyme solution, in particular lysostaphin-lysozyme solution, is performed prior to extraction, in order to increase the sensitivity for the detection of difficultly digestible gram-positive bacteria.

In that it is particularly favorable to amplify a nucleic acid sequence from the highly conserved 16S rDNA region of a bacterial genome, in order to enable a possibly comprehensive detection of different types of bacteria using as few reagents as possible, in particular primer sequences.

With the method according to the invention, a plurality of different physiological samples, like a body fluid from a group encompassing blood, blood fractions, plasma, bone marrow, urine, stool, saliva, lymph, exudates, transudates, secretions, spinal fluid, seminal fluid, dispersed tissue and/or fluids from natural or unnatural body cavities or smears, respectively, can be advantageously analyzed. Thus, no or only a few adaptation steps for samples of a respectively different origin have to be performed.

Particularly preferred, thrombocytes are analyzed as the physiological sample using the method according to the invention. Thrombocyte concentrates are actually responsible for the majority of blood component-associated sepses. The frequency of bacterial contaminations of thrombocytes is relatively high.

Due to the specific probes, it is furthermore possible to distinguish gram-positive and gram-negative bacteria and to allocate them to the respective strains of bacteria or to determine the type of bacteria, respectively, using the fusion temperature.

Preferably, the kit also contains further components, like magnesium chloride solution, bovine serum albumin, buffer and sterile water, whereby matched reagents for detecting various types of bacteria are used and thus an introduction of foreign contaminations with reagents of unknown origin can be avoided.

In particular, the present invention describes a method for detecting bacterial contaminations in physiological fluids.

The sample preparation of the biological sample is performed on the basis of the automated extraction method MagNA Pure Compact Nucleic Acid Isolation Kit—large volume of the company Roche Diagnostics, wherein on the basis of various buffers, the cells are digested and bacterial DNA is released. The DNA is bound to magnetized particles, purified and finally eluted in a special buffer.

In order to achieve a higher efficiency of extraction and to enhance the digestion of the bacteria, prior to extraction, the sample is incubated with a special enzyme solution, a lysostaphin-lysozyme solution.

The lysostaphin-lysozyme solution consists of 100 mg/ml of lysozyme and 5 mg/ml of lysostaphin and water or buffer, respectively, preferably PBS (phosphate-buffered saline).

For example, DNA is isolated from 1000 µl of plasma or thrombocyte concentrate following previous enzyme incubation for enhanced digestion of the bacteria. The biological sample is incubated with 10 µl of lysostaphin-lysozyme solution (concentration of the stock solution: 10 g/ml of lysozyme and 15 mg/ml of lysostaphin) for 30 minutes at 45° C. The released DNA is subsequently bound to the magnetized particles. Following several washing steps, the DNA is eluted with 50 µl of elution buffer.

Additionally, from extraction on, an internal control (pAW109, Applied Biosystems) is included. This internal control included from extraction on is detected using a TaqMan probe (Fam/BHQ-1, oligonucleotide SEQ ID NO:12), wherein the excited Fam molecule emits fluorescence by hydrolysis of the TaqMan probe only, and the emitted fluorescence can be measured by the separation of dye and quencher, wherein the intensity of the emitted fluorescence is directly proportional to the amount of target DNA.

The extracted DNA is subsequently amplified using real-time PCR, wherein the DNA is mixed into the master-mix, amplified in the light cycler and detected with bacteria-specific probes.

The quantification of the PCR products takes place by means of using DNA dyes. The fluorescent dyes are deposited in the DNA, intercalate or bind to the double-strand DNA, respectively, whereby the fluorescence of these dyes increases. The increase of the target DNA therefore correlates with the increase of fluorescence from cycle to cycle. Following completed PCR, a fusion curve analysis can be performed, on the basis of which the specificity can be determined. For a fusion curve analysis, the DNA is fused and then the temperature slowly increased. For the fusion curve analysis, denaturation takes place for 10 sec. at 95° C., then cooling to 50° C. for 30 seconds and continuous increase of the temperature to 80° C. at a speed of 0.2° C./s. With a temperature specific for each sequence, the two hybridization probes are spatially separated from one another, whereby the fluorescence decreases and the fusion temperature can be determined by means of a mathematical derivation.

The detection of the types of bacteria takes place online using real-time PCR. The real-time PCR technology enables a quantitative real-time analysis of the PCR by means of the measurement of laser-induced fluorescent signals. Amplification and analysis are performed in special ultra-fine capillary tubes, preferably with a capacity of 100 µl.

Within the scope of this invention, the term real-time PCR means an amplification method for nucleic acids based on the principle of conventional PCR and additionally offering the possibility of quantification. In the literature, the following designations like real-time PCR, fluorescence hybridization PCR, LightCycler PCR, hybridization sample PCR, FRET-PCR and quantitative PCR are used synonymously. One big advantage of the real-time PCR technology is the reduced contamination risk. The PCR amplificate no longer has to be applied onto an agarose gel, whereby a transfer of contaminations can be avoided and furthermore the confirmation reaction in the PCR run is integrated by the fluorescence-marked hybridization probes.

The quantification is performed by means of fluorescence measurements at the end of or during, respectively, a PCR cycle (real-time) and thus differs from other quantitative PCR methods, which are quantitatively evaluated following the completion of the PCR only (e.g. competitive PCR). The fluorescence increases proportionally to the amount of the PCR products, which enables quantification. The gel-electrophoretic separation of the fragments is not necessary, the data are immediately available, and the risk of contamination is thus low.

To the PCR preparation, beside the specific primers, also at least two sequence-specific hybridization probes or a sequence-specific TaqMan probe are added. The at least one probe binds to a nucleic acid sequence between the two primers and is marked with two different fluorescent dyes. The probe is preferably marked at the 3' terminus with a quencher dye and at the 5' terminus with a fluorescent reporter dye. When the intact probe is excited by light of a predefined wavelength, then the fluorescence emission of the reporter dye is suppressed by the spatial proximity to the quencher dye (FRET principle). The fluorescence intensity of the reporter dye is proportional to the amount of DNA formed. The reporter fluorescence is measured at predefined intervals, without having to open the PCR reaction vessel, and thus the course of the PCR reaction can be followed quite easily. Within the PCR curve, a suitable point for the quantification may be chosen.

For the amplification, a master-mix is prepared, which represents a solution of enzyme (Mol-Taq 16S), sterile water, buffer, magnesium chloride, BSA (bovine serum albumin), dinucleotide triphosphate (dNTPs), primer and probes. Since the enzyme is recombinantly produced in Escherichia coli and no contamination-free enzyme is commercially available, a special Taq polymerase is used, which is re-purified with PCR filter units of the company Millipore.

For example, the master-mix for each sample preparation consists of the components listed in the following and is finally filtered:

| Component | Volume in µl per sample preparation |
|---|---|
| H$_2$O | 11.05 |
| MgCl$_2$ 25 mM | 3 |
| 10x Molzym buffer | 6.25 |
| BSA 20 µg/µl | 0.6 |
| dNTPs 10 mM | 1 |
| MolTaq 16S 5 U/µl | 0.6 |
| Sum | 22.5 µl |

Additionally, 2.5 µl of a 20× detection mix are prepared with the specific hybridization probes for each sample preparation. 25 µl of the finished master-mix are placed in each capillary tube and 25 µl of the biological sample or the negative or positive control, respectively, are added.

The detection mix is prepared as a stock solution and comprises the following components:

| Primers/Probes | Concentration in PCR [µM] | Stock [µM] | Volume [µl] for 100 µl |
|---|---|---|---|
| SEQ ID NO: 1 | 0.3 | 100 | 6 |
| SEQ ID NO: 2 | 0.3 | 100 | 6 |
| SEQ ID NO: 5 | 0.2 | 50 | 8 |
| SEQ ID NO: 6 | 0.2 | 50 | 8 |
| SEQ ID NO: 7 | 0.2 | 50 | 8 |
| SEQ ID NO: 8 | 0.2 | 50 | 8 |
| SEQ ID NO: 9 | 0.2 | 50 | 8 |
| SEQ ID NO: 10 | 0.2 | 50 | 8 |
| SEQ ID NO: 11 | 0.2 | 50 | 8 |
| SEQ ID NO: 3 | 0.2 | 100 | 4 |
| SEQ ID NO: 4 | 0.2 | 100 | 4 |
| SEQ ID NO: 12 | 0.2 | 50 | 8 |
| Σ | | | 84 |
| Water | | | 16 |
| Σ | | | 100 |

The use of the hybridization probes enables the specific detection of the PCR product, non-specific products and primer dimers are not detected.

The hybridization probes SEQ ID NO:5 to SEQ ID NO:35 are marked with different, in particular fluorescent dyes, like e.g. LC 610, LC 640, LC 670, LC 705 and/or fluorescein.

From the amplification with the selected primers in the conserved 16S rDNA region results a 466 base pair PCR product. The selection of the target DNA sequence depends on the highest possible conservation of the sequence considering the various types of bacteria. The bacteria PCR uses the primers SEQ ID NO:1 and SEQ ID NO:2 as well as hybridization probes localized within a highly conserved region of the 16S rDNA of the bacterial genome.

For detection of the gram-positive and gram-negative bacteria as well as for distinction of the types of bacteria, the various hybridization probes SEQ ID NO:5 to SEQ ID NO:11 and SEQ ID NO:13 to SEQ ID NO:35 are used, which are marked with different dyes as well as have different fusion temperatures. The internal control is detected with the probe SEQ ID NO:12.

Oligonucleotides of SEQ ID NO:6 to SEQ ID NO:11 and SEQ ID NO:13 to SEQ ID NO:35 are used as bacteria-specific probes, wherein it will be demonstrated in the following, which of the probes identifies gram-positive or gram-negative, respectively, types of bacteria and/or is specific for which type of bacteria.

| Type of bacteria | gram | Sequence 5'-3' | SEQ ID NO |
|---|---|---|---|
| *Actinomyces israelii* | pos | ACGGTAGCCGGGTTATGAAGCGCCG | 13 |
| *Actinomyces odontolyticus* | pos | AGGGTAGTGGGTAAGAAGCGCCG | 14 |
| *Arcanobacterium haemolyticum* | pos | TGAATAAGCGCCGGCTAAGCGCG | 15 |
| *Bacteroides eggerthii* | neg | ATGTACCGTATGAATAAGGAT | 16 |

-continued

| Type of bacteria | gram | Sequence 5'-3' | SEQ ID NO |
|---|---|---|---|
| Bacteroides fragilis | neg | ATGTATAATATGAATAAGGAT | 17 |
| Bacteroides forsythus | neg | ATGTACCTTGTGAATAAGCAT | 18 |
| Bacteroides merdae | neg | ATGTACCCTATGAATAAGCAT | 19 |
| Bacteroides putredinis | neg | AAGTATCGTACGAATAAGGAT | 20 |
| Chlamydiae trachomatis | neg | AGCGTACCAGGTAAAGAAGCACCG | 21 |
| Chlamydiae pneumonia | neg | AGCGTACCGGGTAAAGAAGCACCG | 22 |
| Fusobacterium sulci | neg | TACCCTTGGAGGAAGCCGCGGCTAACTA | 23 |
| Leptospira biflexa | neg | TACCTACCTAAAGCACCGGCTAACTA | 24 |
| Leptospira interrogans | neg | TACCTGCCTAAAGCACCGGCTAACTA | 25 |
| Mobiluncus mulieris | neg | GGTAGCGGGGGAAGAAGCGCCG | 26 |
| Mycoplasma pmeumoniae | neg | CTGTACCATTTTGAATAAGTGACG | 27 |
| Peptostreptococcus anaerobicus | pos | TACCCTGTGAGGAAGCCCCGGCTAACTA | 28 |
| Peptostreptococcus magnus | pos | TACCATAGGAGGAAGCCCCGGCTAAATA | 29 |
| Porphyromonas endodontalis | neg | CATGTACTCTACGAATAAGTATCG | 30 |
| Rothia dentocariosa | pos | ACGGTAGGTGCAGAGAAAGCGCCG | 31 |
| Sphingobacterium multivorum | neg | CTGAATGTACTGGAAGAATAAGGATCG | 32 |
| Sphingobacterium spiritivorum | neg | CTGAATGTACCCAAGAATAAGGATCG | 33 |
| Treponema pallidum | neg | ACGGTAGTCGTGCGAATAAGCCCCG | 34 |
| Ureaplasma urealyticum | neg | ACTGTACCATTTGAATAAGTATCG | 35 |
| | pos | TAGTTAGCCGTGGCTTTCTGGTTAGATA | 6 |
| | pos | TAGTTAGCCGTCCCTTTCTGGTTAGATA | 7 |
| | pos | TAGTTAGCCGTGGCTTTCTGGTTAGGTA | 8 |
| | neg | CGGTGCTTCTTCTGCGAGTAAC | 9 |
| | neg | CGGTGCTTATTCTTTAGGTACCGT | 10 |
| | neg | CGGTGCTTATTCTGTTGGTAACGT | 11 |

The oligonucleotides of SEQ ID NO:6 to SEQ ID NO:11 partially detect, as described in the above table, gram-positive as well as gram-negative types of bacteria. Which type of bacteria they specifically detect will be described in the following.

The oligonucleotides SEQ ID NO:6 specifically detect the genera *Enterococcus, Kurthia, Lactobacillus* and/or *Listeria* and selectively detect *Enterococcus avium, Enterococcus casseliflavus, Enterococcus durans, Enterococcus faecalis, Enterococcus faecium, Enterococcus gallinarum, Enterococcus hirae, Kurthia gibsonii, Kurthia sibirica, Lactobacillus acidophilus, Lactobacillus casei, Lactobacillus fermentum, Lactobacillus plantarum, Lactobacillus salivarius, Listeria monocytogenes, Listeria pyogenes,* preferably in a physiological sample.

Oligonucleotides of SEQ ID NO:7 specifically detect the genera *Leuconostoc* and/or *Streptococcus* and selectively detect *Leuconostoc citreum, Leuconostoc lactis, Streptococcus agalactiae, Streptococcus anginosus, Streptococcus bovis, Streptococcus mitis, Streptococcus pneumoniae, Streptococcus pyogenes, Streptococcus salivarius, Streptococcus sanguinis and/or Streptococcus sp., preferably in a physiological sample.

The genera Bacillus, Clostridium, Mycoplasma and/or Staphylococcus are specifically detected by oligonucleotide SEQ ID NO:8. Selectively detected with oligonucleotide SEQ ID NO:8 are Bacillus anthracis, Bacillus circulans, Bacillus pumilus, Bacillus sphaericus, Bacillus subtilis, Bacteroides capillosus, Brevibacillus laterosporus, Clostridium bifermentans, Clostridium botulinum, Clostridium butyricum, Clostridium clostridioforme, Clostridium difficile, Clostridium novyi, Clostridium perfringens, Clostridium septicum, Clostridium sporogenes, Clostridium tetani, Erysipelothrix rhusiopathiae, Fusobacterium alocis, Gemella haemolysans, Mycoplasma orale, Mycoplasma pulmonis, Mycoplasma buccale, Staphylococcus aureus, Staphylococcus capitis, Staphylococcus cohnii, Staphylococcus epidermidis, Staphylococcus haemolyticus, Staphylococcus hominis, Staphylococcus lugdunensis, Staphylococcus xylosus and/or Veillonella parvula, preferably in a physiological sample.

The oligonucleotides SEQ ID NO:9 specifically detect the genera Acinetobacter, Actinomyces, Aeromonas, Anaerobiospirillum, Bartonella, Brucella, Citrobacter, Enterobacter, Haemophilus, Klebsiella, Kluyvera, Legionella, Pasteurella, Proteus, Rickettsia, Salmonella, Serratia, Shigella, Vibrio, Yersinia, and selectively detect Acinetobacter baumannii, Acinetobacter calcoaceticus, Acinetobacter haemolyticus, Acinetobacter johnsonii, Acinetobacter junii, Acinetobacter lwoffii, Actinomyces meyeri, Actinomyces pyogenes, Aeromonas caciae, Aeromonas hydrophila, Aeromonas schubertii, Aeromonas veronii, Agrobacterium radiobacter, Alcaligenes faecalis, Anaerobiospirillum succiniciproducens, Anaerobiospirillum thomasii, Acranobacterium pyogenes, Bartonella bacilliformis, Bartonella henselae, Brucella abortus, Brucella melitensis, Calymmatobacterium granulomatis, Citrobacter amalonaticus, Citrobacter freundii, Coxiella burnetti, Edwardsiella tarda, Enterobacter aerogenes, Enterobacter cloacae, Enterobacter sakazakii, Enterobacter sp., Escherichia coli, Haemophilus aegypticus, Haemophilus aphrophilus, Haemophilus ducreyi, Haemophilus parahaemolyticus, Haemophilus parainfluenzae, Haemophilus paraphrophilus, Haemophilus segnis, Hafnia alvei, Klebsiella oxytoca, Klebsiella pneumoniae, Klebsiella rhinoscleromatis, Kluyvera ascorbata, Kluyvera cryocrescens, Legionella dumoffii, Legionella micdadei, Morganella morganii, Ochrobactrum anthropi, Pantoea agglomerans, Pasteurella gallinarum, Pasteurella pneumotropica, Plesiomonas shigelloides, Propionibacterium acnes, Proteus mirabilis, Proteus penneri, Proteus vulgaris, Pseudomonas putida, Rickettsia akari, Rickettsia australis, Rickettsia conorii, Salmonella choleraesius, Salmonella enterica, Salmonella paratyphi A, Salmonella paratyphi B, paratyphi C, Salmonella typhi, Salmonella typhinurium, Serratia ficaria, Serratia fonticola, Serratia grimesii, Serratia liquefaciens, Serratia marcescens, Serratia rudidaea, Shigella boydii, Shigella dysenteriae, Shigella flexneri, Shigella sonnei, Vibrio alginolyticus, Vibrio hollisae, Wigglesworthia glossinidia, Xanthomonas campestris, Yersinia enterocolitica, Yersinia pestis and/or Yersinia pseudotuberculosis, preferably in a physiological sample.

Oligonucleotide SEQ ID NO:10 specifically detects the genera Achromobacter, Actinomadura, Actinomyces, Afipia, Bordetella, Burkholderia, Campylobacter, Capnocytophaga, Comamonas, Corynebacterium, Ehrlichia, Fusobacterium, Methylobacterium, Mycobacterium, Neisseria, Nocardia, Oligella, Prevotella and/or Rhodococcus and selectively detects Achromobacter piechaudii, Achromobacter xylosoxidans, Actinomadura madurae, Actinomadura pelletieri, Actinomyces bovis, Actinomyces naeslundii, Actinomyces viscosus, Afipia broomeae, Afipia felis, Bacteroides gracilis, Bilophila wadsworthia, Bordetella bronchiseptica, Bordetella parapertussis, Bordetella pertussis, Burkholderia cepacia, Burkholderia gladioli, Burkholderia mallei, Burkholderia pseudomallei, Campylobacter coli, Campylobacter fetus, Campylobacter jejuni, Campylobacter lari, Capnocytophaga canimorsus, Capnocytophaga cynodegmi, Capnocytophaga gingivalis, Capnocytophaga ochracea, Capnocytophaga sputigena, Chromobacterium violaceum, Comamonas terrigena, Comamonas testosteroni, Corynebacterium diphteriae, Corynebacterium minutissimum, Corynebacterium pseudotuberculosis, Corynebacterium urealyticum, Ehrlichia canis, Ehrlichia chaffeensis, Ehrlichia sennetsu, Eikenella corrodens, Eubacterium lentum, Francisella tularensis, Fusobacterium necrophorum, Fusobacterium nucleatum, Gardnerella vaginalis, Haemophilus influenzae, Helicobacter pylori, Kingella kingae, Methylobacterium extorquens, Methylobacterium mesophilicun, Mycobacterium africanum, Mycobacterium avium, Mycobacterium bovis, Mycobacterium chelonae, Mycobacterium intracellulare, Mycobacterium kanasasii, Mycobacterium leprae, Mycobacterium malmoense, Mycobacterium marinum, Mycobacterium scrofulaceum, Mycobacterium tuberculosis, Mycobacterium xenopi, Neisseria cinerea, Neisseria gonorrhoeae, Neisseria meningitidis, Nocardia asteroides, Nocardia nova, Nocardia octitidiscaviarum, Oligella urethralis, Oligella ureulytica, Peptoniphilus asaccharolyticus, Peptostreptococcus prevotii, Porohyromonas gingivalis, Prevotella buccae, Prevotella buccalis, Prevotella corporis, Prevotella denticola, Prevotella oralis, Rhodococcus equi, Rhodococcus erythropolis, Rhodococcus rhodochrous, Stenotrophomonas maltophilia, Streptobacillus moniliformis, Tropheryma whippley and/or Weeksella virosa, preferably in a physiological sample.

The genera Actinobacillus, Borrelia, Legionella, Moraxella (Branhamella), Providencia, Pseudomonas and/or Vibrio are specifically detected by oligonucleotide SEQ ID NO:11, which selectively detects Actinobacillus actinomycetemcomitans, Actinobacillus equuli, Actinobacillus hominis, Actinobacillus suis, Actinobacillus ureae, Borrelia afzelii, Borrelia burgdorferi, Borrelia garninii, Borrelia hermsii, Borrelia hispanica, Chryseomonas luteola, Legionella dumoffii, Legionella micdadei, Legionella pneumophila, Moraxella (Branhamella) catarrhalis, Moraxella (Branhamella) nonliquefaciens, Moraxella (Branhamella) osloensis, Moraxella (Branhamella) phenylpyruvica, Pediococcus pentosaceus, Porphyromonas asaccharolytica, Providencia alcalifaciens, Providencia rettgeri, Providencia rustigianii, Providencia stuartii, Pseudomonas aeruginosa, Pseudomonas fluorescense, Psychrobacter immobilis, Vibrio cholerae, Vibrio parahaemolyticus and/or Vibrio vulnificus, preferably in a physiological sample.

The amplification of the biological samples to be analyzed and of the negative, positive and internal controls passes through the following PCR program:

The biological sample is denatured for 4 minutes at 95° C. in advance, followed by 45 cycles, wherein in each cycle denaturation takes place at 95° C. for 5 seconds, annealing at 60° C. for 25 seconds and extension for 40 seconds at 72° C. For the fusion curve, denaturation is performed for 10 seconds at 95° C., cooling for 30 seconds to 50° C. and continuous increase of the temperature to 80° C. with a speed of 0.2° C./s.

During the entire workflow, positive controls—namely *Staphylococcus epidermidis* 1000 cfu/ml, *Pseudomonas aeruginosa* 2000 cfu/ml and *Salmonella choleraesius* 2000 cfu/ml—and one negative control (human thrombocyte concentrate) are included. In order to be able to determine a possible inhibition, pAW109 cDNA is co-amplified as internal control in each reaction preparation. The detection limit for the individual types of bacteria is >5 cfu/ml.

The negative control and the positive control *Staphylococcus epidermidis* 1000 cfu/ml are included from extraction on, and the two further positive controls *Salmonella choleraesius* 2000 cfu/ml and *Pseudomonas aeruginosa* 2000 cfu/ml from amplification on only.

For the preparation of the positive control with *Staphylococcus epidermidis*, centrifuged off thrombocyte concentrate and a bacterial suspension at a concentration of 1000 cfu/ml are pipetted at a ratio of approximately 4:1.

For the preparation of the positive control with *Salmonella choleraesius* 2000 cfu/ml, for example thrombocyte concentrate and the bacterial suspension are mixed at a ratio of approximately 2:1. Furthermore, to 1 ml of positive control, 10 ml of lysozyme-lysostaphin solution is added, then mixed and preferably incubated at 45° C.

The preparation of the positive control of *Pseudomonas aeruginosa* is performed like that of *Salmonella choleraesius*.

Subsequently, extraction is performed on MagNa Pure Compact adding the internal control pAW 109.

As internal control, GeneAmpRNA pAW109 is used from extraction on, which is transcribed into cDNA, subsequently amplified, diluted and purified, preferably with ExoSap and Microcon filtration, before it is used as the control for clinical analyses. The internal control is then added to the physiological samples and included from extraction on. The internal control is co-amplified by means of specific primers—SEQ ID NO:3 and SEQ ID NO:4—in the reaction preparation and serves as workflow control. The forward primer used for amplification has at least 10 consecutive bases of the sequence SEQ ID NO:1 5'-tcctacgggaggcagcagt-3' and the backward primer 10 consecutive bases of the sequence SEQ ID NO:2 5'-ggactaccagggtatctaatcctgtt-3'.

For detection of the internal control, a Fam/BHQ-1-marked TaqMan probe is admixed to the amplification mix, wherein the excited Fam molecule emits fluorescence upon hydrolysis of the TaqMan probe only, and the emitted fluorescence can be measured by the separation of dye and quencher, wherein the intensity of the emitted fluorescence is directly proportional to the amount of target DNA. The probes SEQ ID NO:6 to SEQ ID NO:11 and SEQ ID NO:13 to SEQ ID NO:35 may likewise be used as TaqMan probes.

If the two fluorescent dyes (e.g. Tamra or Fam of the 5' terminus and BHQ-1 of the 3' terminus) of the TaqMan probe are close to one another, following excitation, for example with a laser, the energy of the reporter dye is transferred to the quencher dye, which then emits light. During the PCR, both primers are elongated by means of polymerase until they contact the probe. There, the hybridized DNA probe is removed from the DNA strand and decomposed by means of the 5' to 3' exonuclease activity of the polymerase. With the hydrolysis of the probe, the spatial proximity between reporter and quencher is interrupted and an increasing fluorescence of the reporter dye can be measured. A hydrolysis of the probe by the 5' to 3' exonuclease activity may only take place, if there is a sequence-specific hybridization between probe and target sequence. According to the amplification of the specific PCR fragment, the fluorescent signal increases. In that, the fluorescence increase is directly proportional to the increase of PCR amplificates.

With the internal control, a variation in extraction or insufficient amplification can be determined. The amplificate is characterized by a length of approximately 60 base pairs. A FamBHQ-1-marked TaqMan probe hybridizes with the template. The signal is read in channel 530 and analyzed (as described in more detail in the following). The sequence of the Fam-BHQ-1-marked TaqMan probe is SEQ ID NO:12.

The amplification of the internal control takes place in a solution consisting of water, Mn, enzyme mix, primers of SEQ ID NO:3 and SEQ ID NO:4 as well as the probe of SEQ ID NO:12. In particular, the concentrations and volumes for the master mix are the following: 3.5 µl of water, 1 µl of 50 mM Mn, 7.5 µl of 2.7× enzyme mix, 1 µl of 5 mM primers SEQ ID NO:3 and SEQ ID NO:4 each and 1 µl of 5 mM probe SEQ ID NO:12. 15 µl of the master mix are pipetted to 5 µl of the positive control and reversely transcribed and amplified. The reverse transcription takes place for 30 minutes at 60° C. For amplification, the sample is denatured for 8 minutes at 95° C. in advance and subsequently amplified in 45 cycles of 15 seconds at 95° C., 1 minute at 60° C. and 1 minute at 40° C. each.

An inhibition by positive amplification of the internal control can be excluded.

The evaluation by means of fusion curves enables a distinction of gram-positive and gram-negative bacteria and an allocation to types of bacteria on the basis of the fusion temperature of the hybridization probes of the amplified DNA. Fusion curve analyses are performed at the end of the PCR. In that, a temperature curve, starting at 50° C., up to 80° C. is performed and recorded. In that, at a certain temperature point, the probes detach themselves from the bacterial DNA and the fluorescence decreases. The integration of the fluorescence by the temperature results in a fusion peak, which can be consulted for the evaluation of the results.

The assessment and evaluation of the wild type samples exclusively takes place with fusion curve analysis by means of a cut-off determined following validation. Due to bacterial contaminations occurring very easily during the workflow or by the enzyme, respectively, this cut-off in the fusion curve analysis is determined at a fluorescent signal of >0.03. The evaluation of the internal control takes place by means of absolute quantification analysis.

For an unambiguous evaluation of all channels, a Multi-ColorDemo kit color compensation has to be imported in order to switch off the crosstalk between the channels.

Following completion of the PCR, the individual channels are evaluated as follows and the internal control and the positive controls checked:

Channel 530: internal control pAW109;
Channel 610: *Staphylococcus epidermidis* 1000 cfu/ml (gram-positive) *Staphylococcus aureus* 1000 cfu/ml (gram-positive)
Channel 640: *Salmonella choleraesius* 2000 cfu/ml (gram-negative)
Channel 705: *Pseudomonas aeruginosa* 2000 cfu/ml (gram-negative)

In channel 530, all samples must have a positive curve increase. In channel 610, gram-positive bacteria are detected. The positive control *Staphylococcus epidermidis* must have an unambiguous curve progression with a fluorescence value of ~0.55 in the fusion curve analysis. In addition, this fluorescence value is also used as a function test of the lysozyme-lysostaphin digestion.

Gram-negative bacteria are analyzed and detected in channel 640, wherein *Salmonella choleraesius* must have an unambiguous curve progression with a fluorescence value of ~0.6 in the fusion curve analysis.

In channel 705, too, gram-negative bacteria are detected. The positive control *Pseudomonas aeruginosa* must show an unambiguous curve progression with a fluorescence value of ~0.8 in the fusion curve analysis.

A clear increase in the fusion curve of a biological sample to be examined in one of the 4 channels, which has a fluorescence >0.03, is considered positive. Such samples are re-extracted and re-amplified in clinical routine, in order to be able to make a relevant statement.

Subsequently, by way of example, the fusion temperatures and channels of individual types of bacteria are listed:

| Type of bacteria | Type | Fusion temperature | Channel |
| --- | --- | --- | --- |
| Pseudomonas aeruginosa | gram-negative | 68.5 | 705 |
| Salmonella choleraesius | gram-negative | 62.5 | 640 |
| Staphylococcus epidermidis | gram-positive | 68 | 610 |
| Enterococcus faecalis | gram-positive | 71 | 610 |
| Clostridium sporogenes | gram-positive | 60.8 | 610 |
| Lactobacillus fermentum | gram-positive | 64.6 | 610 |
| Staphylococcus aureus | gram-positive | 67.5 | 610 |
| Bacillus subtilis | gram-positive | 71.5 | 610 |

Furthermore, the fusion curve of channel 670 is also evaluated for sample analysis. The examination of the internal control takes place via channel 530 by means of the crossing points in the quantification analysis.

The evaluation of the analysis takes place by means of the so-called CT value (threshold cycle). The CT value expresses the number of cycles, at which an increase of the reporter fluorescence above the background noise is determined for the first time.

The detection of the internal control is based on the TaqMan principle described already, wherein the excited Fam molecule at the 5' terminus of the oligonucleotide SEQ ID NO:12 only emits the light in channel 530 with the hydrolysis of the TaqMan probe. Only with the separation of reporter and quencher dye the emitted light can be measured. The intensity of the light emitted is directly proportional to the amount of target DNA.

The positive controls in the various channels show a function graph with a peak at the following temperatures:

| Type of bacteria | Channel | Fusion temperature in ° C. |
| --- | --- | --- |
| Staphylococcus aureus | 610 | 67.5 |
| Escherichia coli | 640 | 62 |
| Pseudomonas aeruginosa | 705 | 68.5 |

Finally, it has to be pointed out, that individual properties or combinations of properties from the different embodiments demonstrated and described may represent independent, inventive solutions or solutions according to the invention as well.

Any details on value ranges in the present description have to be understood that way that they also comprise any and all sub-ranges thereof, e.g. the detail 1 to 10 has to be understood that way that any sub-ranges, starting from the lower limit 1 and up to the upper limit 10 are also comprised, i.e. any sub-ranges start with a lower limit of 1 or higher and end with an upper limit of 10 or less, e.g. 1 to 1.7 or 3.2 to 8.1 or 5.5 to 10.

The embodiments show possible embodiment variants of the composition, wherein it has to be pointed out at this point, that the invention is not limited to the especially represented embodiments thereof, but that rather diverse combinations of the individual embodiments among one another are possible, too, and that due to the directive for technical actions this possibility for variation by the present invention lies within the skill of the skilled person in this technical field. The scope of protection thus also includes any perceivable embodiments, which are possible by combinations of individual details of the embodiment variant represented and described.

The invention claimed is:

1. A method for detecting at least one type of bacterial contamination in a physiological sample comprising human cells said method comprising the steps of i) extracting bacterial DNA from said physiological sample, ii) amplifying said bacterial DNA by real-time PCR using an oligonucleotide primer pair, said oligonucleotide primer pair consisting of an oligonucleotide comprising at least 10 consecutive bases of SEQ ID NO:1 and an oligonucleotide comprising at least 10 consecutive bases of SEQ ID NO:2, thereby producing amplified bacterial DNA, and hybridizing said amplified bacterial DNA with at least two oligonucleotide hybridization probes, wherein one of said at least two oligonucleotide hybridization probes comprises at least 10 consecutive bases of SEQ ID NO:5 and is marked with fluorescein at the 3' terminus, and at least one of said at least two oligonucleotide hybridization probes is selected from the group consisting of SEQ ID NO:6-SEQ ID NO:11 and is marked with a fluorescent dye at the 5' terminus and iii) evaluating the amplified bacterial DNA from step ii) by means of fusion curve analysis, thus detecting if present at least one type of bacterial contamination in said physiological sample; and wherein said method further comprises detecting at least one internal control, wherein nucleic acid for said at least one internal control is added to the bacterial DNA after said extracting step (i), and said nucleic acid for said at least one internal control is co-amplified with the bacterial DNA in step (ii); and wherein said nucleic acid of said at least one internal control is is co-amplified in step (ii) with an oligonucleotide primer pair, said oligonucleotide primer pair comprising an oligonucleotide comprising at least 10 consecutive bases of SEQ ID NO:3 and an oligonucleotide comprising at least 10 consecutive bases of SEQ ID NO:4.

2. The method according to claim 1, wherein said extracting step (i) comprises lysing bacterial cells to release said bacterial DNA, binding said bacterial DNA to magnetized particles, purifying said bacterial DNA, and eluting said purified bacterial DNA with a buffer.

3. The method according to claim 1, wherein said method further comprises incubating said physiological sample with a lysostaphin-lysozyme solution before said extracting step (i).

4. The method according to claim 1, wherein said amplifying step (ii) using said oligonucleotide primer pair consisting of an oligonucleotide comprising at least consecutive bases of SEQ ID NO:1 and an oligonucleotide comprising at least 10 consecutive bases of SEQ ID NO:2 results in the amplification of a region of 16S rDNA in the bacterial genome.

5. The method according to claim 1,
further comprising detecting, in addition to said internal control, at least one negative control and/or at least one positive control.

6. The method according to claim 5, wherein said detecting at least one positive control comprises amplifying and detecting a nucleic acid sequence of *Salmonella choleraesius*, *Pseudomonas aeruginosa* and/or *Staphylococcus epidermidis*.

7. The method according to claim 1, wherein co-amplified amplification products of said at least one internal control are hybridized with an oligonucleotide hybridization probe comprising at least 10 consecutive bases of SEQ ID NO:12, or its complementary sequence, during the amplifying step (ii).

8. The method according to claim 1, wherein the real-time PCR is performed in capillary tubes.

9. The method according to claim 1, wherein said physiological sample is a body fluid selected from the group consisting of blood, blood fractions, plasma, bone marrow, urine, stool, saliva, lymph, exudates, transudates, secretions, spinal fluid, seminal fluid, dispersed tissue and/or fluids from natural or non-natural body cavities or smears.

10. The method according to claim 1, wherein said human cells are thrombocytes.

11. The method according to claim 1, wherein gram-positive bacterial contamination is detected in said physiological sample, and is thus distinguished from gram-negative bacterial contamination.

12. The method according to claim 1, wherein the types of bacterial contamination detected by said fusion curve analysis are selected from the group consisting of *Enterococcus avium*, *Enterococcus casseliflavus*, *Enterococcus durans*, *Enterococcus faecalis*, *Enterococcus faecium*, *Enterococcus gallinarum*, *Enterococcus hirae*, *Kurthia gibsonii*, *Kurthia sibirica*, *Lactobacillus acidophilus*, *Lactobacillus casei*, *Lac-* tobacillus fermentum, Lactobacillus plantarum, Lactobacillus salivarius, Listeria monocytogenes, Listeria pyogenes, Leuconostoc citreum, Leuconostoc lactis, Streptococcus agalactiae, Streptococcus anginosus, Streptococcus bovis, Streptococcus mitis, Streptococcus pneumoniae, Streptococcus pyogenes, Streptococcus salivarius, Streptococcus sanguinis, Streptococcus sp., Bacillus anthracia, Bacillus circulans, Bacillus pumilus, Bacillus sphaericus, Bacillus subtilis, Bacteroides capillosus, Brevibacillus laterosporus, Clostridium bifermentans, Clostridium botulinum, Clostridium butyricum, Clostridium clostridioforme, Clostridium difficile, Clostridium novyi, Clostridium perfringens, Clostridium septicum, Clostridium sporogenes, Clostridium tetani, Erysipelothrix rhusiopathiae, Fusobacterium alocis, Gemella haemolysans, Mycoplasma orale, Mycoplasma pulmonis, Mycoplasma buccale, Staphylococcus aureus, Staphylococcus capitis, Staphylococcus cohnii, Staphylococcus epidermidis, Staphylococcus haemolyticus, Staphylococcus hominis, Staphylococcus lugdunensis, Staphylococcus xylosus, Veillonella parvula, Acinetobacter baumannii, Acinetobacter calcoaceticus, Acinetobacter haemolyticus, Acinetobacter johnsonii, Acinetobacter junii, Acinetobacter lwoffii, Actinomyces meyeri, Actinomyces pyogenes, Aeromonas caciae, Aeromonas hydrophila, Aeromonas schubertii, Aeromonas veronii, Agrobacterium radiobacter, Alcaligenes faecalis, Anaerobiospirillum succiniciproducens, Anaerobiospirillum thomasii, Acranobacterium pyogenes, Bartonella bacilliformis, Bartonella henselae, Brucella abortus, Brucella melitensis, Calymmatobacterium granulomatis, Citrobacter amalonaticus, Citrobacter freundii, Coxiella burnetti, Edwardsiella tarda, Enterobacter aerogenes, Enterobacter cloacae, Enterobacter sakazakii, Enterobacter sp., Escherichia coli, Haemophilus aegypticus, Haemophilus aphrophilus, Haemophilus ducreyi, Haemophilus parahaemolyticus, Haemophilus parainfluenzae, Haemophilus paraphrophilus, Haemophilus segnis, Hafnia alvei, Klebsiella oxytoca, Klebsiella pneumoniae, Klebsiella rhinoscleromatis, Kluyvera ascorbata, Kluyvera cryocrescens, Legionella dumoffii, Legionella micdadei, Morganella morganii, Ochrobactrum anthropi, Pantoea agglomerans, Pasteurella gallinarum, Pasteurella pneumotropica, Plesiomonas shigelloides, Propionibacterium acnes, Proteus mirabilis, Proteus penneri, Proteus vulgaris, Pseudomonas putida, Rickettsia akari, Rickettsia australis, Rickettsia conorii, Salmonella choleraesius, Salmonella enterica, Salmonella paratyphi A, Salmonella paratyphi B, Salmonella paratyphi C, Salmonella typhi, Salmonella typhinurium, Serratia ficaria, Serratia fonticola, Serratia grimesii, Serratia liquefaciens, Serratia marcescens, Serratia rudidaea, Shigella boydii, Shigella dysenteriae, Shigella flexneri, Shigella sonnei, Vibrio alginolyticus, Vibrio hollisae, Wigglesworthia glossinidia, Xanthomonas campestris, Yersinia enterocolitica, Yersinia pestis, Yersinia pseudotuberculosis, Achromobacter piechaudii, Achromobacter xylosoxidans, Actinomadura madurae, Actinomadura pelletieri, Actinomyces bovis, Actinomyces naeslundii, Actinomyces viscosus, Afipia broomeae, Afipia felis, Bacteroides gracilis, Bilophila wadsworthia, Bordetella bronchiseptica, Bordetella parapertussis, Bordetella pertussis, Burkholderia cepacia, Burkholderia gladioli, Burkholderia mallei, Burkholderia pseudomallei, Campylobacter coli, Campylobacter fetus, Campylobacter jejuni, Campylobacter lari, Capnocytophaga canimorsus, Capnocytophaga cynodegmi, Capnocytophaga gingivalis, Capnocytophaga ochracea, Capnocytophaga sputigena, Chromobacterium violaceum, Comamonas terrigena, Comamonas testosteroni, Corynebacterium diphteriae, Corynebacterium minutissimum, Corynebacterium pseudotuberculosis, Corynebacterium urealyticum, Ehrlichia canis, Ehrlichia chaffeensis, Ehrlichia sennetsu, Eikenella corrodens, Eubacterium lentum, Francisella tularensis, Fusobacterium necrophorum, Fusobacterium nucleatum, Gardnerella vaginalis, Haemophilus influenzae, Helicobacter pylori, Kingella kingae, Methylobacterium extorquens, Methylobacterium mesophilicun, Mycobacterium africanum, Mycobacterium avium, Mycobacterium bovis, Mycobacterium chelonae, Mycobacterium intracellulare, Mycobacterium kanasasii, Mycobacterium leprae, Mycobacterium malmoense, Mycobacterium marinum, Mycobacterium scrofulaceum, Mycobacterium tuberculosis, Mycobacterium xenopi, Neisseria cinerea, Neisseria gonorrhoeae, Neisseria meningitidis, Nocardia asteroides, Nocardia nova, Nocardia octitidiscaviarum, Oligella urethralis, Oligella ureulytica, Peptoniphilus asaccharolyticus, Peptostreptococcus prevotii, Porohyromonas gingivalis, Prevotella buccae, Prevotella buccalis, Prevotella corporis, Prevotella denticola, Prevotella oralis, Rhodococcus equi, Rhodococcus erythropolis, Rhodococcus rhodochrous, Stenotrophomonas maltophilia, Streptobacillus moniliformis, Tropheryma whippley, Weeksella virosa, Actinobacillus actinomycetemcomitans, Actinobacillus equuli, Actinobacillus hominis, Actinobacillus suis, Actinobacillus ureae, Borrelia afzelii, Borrelia burgdorferi, Borrelia garninii, Borrelia hermsii, Borrelia hispanica, Chryseomonas luteola, Legionella dumoffii, Legionella micdadei, Legionella pneumophila, Moraxella (Branhamella) catarrhalis, Moraxella (Branhamella) nonliquefaciens, Moraxella (Branhamella) osloensis, Moraxella (Branhamella) phenylpyruvica, Pediococcus pentosaceus, Porphyromonas asaccharolytica, Providencia alcalifaciens, Providencia rettgeri, Providencia rustigianii, Providencia stuartii, Pseudomonas aeruginosa, Pseudomonas fluorescense, Psychrobacter immobilis, Vibrio cholerae, Vibrio parahaemolyticus, Vibrio vulnificus, Actinomyces israelii, Actinomyces odontolyticus, Arcanobacterium haemolyticum, Bacteroides eggerthii, Bacteroides fragilis, Bacteroides forsythus, Bacteroides merdae, Bacteroides putredinis, Chlamydiae trachomatis, Chlamydiae pneumoniae, Fusobacterium sulci, Leptospira biflexa, Leptospira interrogans, Mobiluncus mulieris, Mycoplasma pneumoniae, Peptostreptococcus anaerobicus, Peptostreptococcus magnus, Porphyromonas endodontalis, Rothia dentocariosa, Sphingobacterium multivorum, Sphingobacterium spiritovorum, Treponema pallidum and Ureaplasma urealyticum.

13. The method according to claim 12, wherein said types of bacterial contamination are detected by evaluating a cut-off fluorescence value in the fusion curve analysis performed during said evaluating step (iii), wherein said cut-off fluorescence value is >0.03, and wherein an increase in fluorescence value >0.03 is considered positive for said types of bacterial contamination in said physiological sample.

14. The method according to claim 1, wherein gram-negative bacterial contamination is detected in said physiological sample, and is thus distinguished from gram-positive bacterial contamination.

* * * * *

SEQUENCE LISTING

<160> NUMBER OF SEQ ID NOS: 35

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcctacggga ggcagcagt                                                19

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggactaccag ggtatctaat cctgtt                                        26

<210> SEQ ID NO 3

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcctgggttc cctgttcc                                                       18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgacgtaccc ctgacatgg                                                      19

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gtattaccgc ggctgctggc ac                                                  22

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tagttagccg tggctttctg gttagata                                            28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tagttagccg tccctttctg gttagata                                            28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tagttagccg tggctttctg gttaggta                                            28

<210> SEQ ID NO 9
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 9
cggtgcttct tctgcgagta ac                                               22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cggtgcttat tctttaggta ccgt                                             24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cggtgcttat tctgttggta acgt                                             24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
caggccaatg tctcaccaag ctctg                                            25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
acggtagccg ggttatgaag cgccg                                            25

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
agggtagtgg gtaagaagcg ccg                                              23

<210> SEQ ID NO 15
<211> LENGTH: 23
<212> TYPE: DNA
<213> ORGANISM: Artificial Sequence
<220> FEATURE:
```

-continued

```
<223> OTHER INFORMATION: Description of Artificial Sequence: Synthetic
      probe

<400> SEQUENCE: 15
tgaataagcg ccggctaagc gcg                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
atgtaccgta tgaataagga t                                                21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
atgtataata tgaataagga t                                                21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
atgtaccttg tgaataagca t                                                21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
atgtaccctA tgaataagca t                                                21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aagtatcgta cgaataagga t                                                21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 21
agcgtaccag gtaaagaagc accg                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
agcgtaccgg gtaaagaagc accg                                              24

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23 taccccttgga ggaagccgcg gctaacta                                         28

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tacctaccta aagcaccggc taacta                                            26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tacctgccta aagcaccggc taacta                                            26

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ggtagcgggg gaagaagcgc cg                                                22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

```
ctgtaccatt ttgaataagt gacg                                          24
```

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28

```
taccctgtga ggaagccccg gctaacta                                      28
```

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29

```
taccatagga ggaagccccg gctaaata                                      28
```

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30

```
catgtactct acgaataagt atcg                                          24
```

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31

```
acggtaggtg cagagaaagc gccg                                          24
```

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32

```
ctgaatgtac tggaagaata aggatcg                                       27
```

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33

```
ctgaatgtac ccaagaataa ggatcg                                        26
```

```
<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
acggtagtcg tgcgaataag ccccg                                          25

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
actgtaccat ttgaataagt atcg                                           24
```